(12) United States Patent
Ebina et al.

(10) Patent No.: US 10,456,602 B2
(45) Date of Patent: Oct. 29, 2019

(54) PARTICLE THERAPY SYSTEM

(71) Applicant: Hitachi, Ltd., Tokyo (JP)

(72) Inventors: Fuutarou Ebina, Tokyo (JP);
Takamichi Aoki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/963,281

(22) Filed: Apr. 26, 2018

(65) Prior Publication Data

US 2018/0326226 A1 Nov. 15, 2018

(30) Foreign Application Priority Data

May 12, 2017 (JP) .................................. 2017-095157

(51) Int. Cl.

| A61N 5/10 | (2006.01) |
|---|---|
| H05H 13/04 | (2006.01) |
| H05H 7/04 | (2006.01) |
| H05H 7/00 | (2006.01) |

(52) U.S. Cl.
CPC ........... *A61N 5/1081* (2013.01); *H05H 7/001* (2013.01); *H05H 7/04* (2013.01); *H05H 13/04* (2013.01); *A61N 5/1049* (2013.01); *A61N 2005/1087* (2013.01); *H05H 2007/002* (2013.01); *H05H 2007/008* (2013.01); *H05H 2007/043* (2013.01); *H05H 2007/048* (2013.01); *H05H 2277/11* (2013.01)

(58) Field of Classification Search
CPC ........ A61N 5/1081; H05H 7/001; H05H 7/04; H05H 13/04; H05H 2007/002; H05H 2007/008; H05H 2007/043; H05H 2007/048; H05H 2277/11

USPC .... 250/492.1, 492.2, 492.3, 396 R, 396 ML, 250/398
See application file for complete search history.

(56) References Cited

FOREIGN PATENT DOCUMENTS

| EP | 1 041 579 A1 | 10/2000 |
|---|---|---|
| EP | 2 777 766 A1 | 9/2014 |
| WO | 2008/081480 A1 | 7/2008 |
| WO | 2013/069379 A1 | 5/2013 |

OTHER PUBLICATIONS

Extended European Search Report received in corresponding European Application No. 18170849.6 dated Oct. 19, 2018.
Benedikt, M. et al., "Matching to Gantries for Medical Synchrotrons", Proceedings of the 1997 Particle Accelerator Conference, May 12-16, 1997, pp. 1379-1381, vol. 2.

*Primary Examiner* — Nicole M Ippolito
*Assistant Examiner* — Hanway Chang
(74) *Attorney, Agent, or Firm* — Mattingly & Malur, PC

(57) ABSTRACT

A particle therapy system capable of reducing the installation area and also suppressing a variation in the irradiation beam position is provided. A synchrotron generates a charged particle beam, and a beam delivery system irradiates an irradiation target with a charged particle beam extracted from the synchrotron thereby forming a radiation field. A rotating gantry is provided with the beam delivery system and is rotatable around the irradiation target. Dispersion measuring devices, each of which measures the dispersion of the charged particle beam at the position of the irradiation target at a plurality of rotation angles of the rotating gantry, are also provided. The orbit center of the charged particle beam extracted from the synchrotron and the rotation axis of the rotating gantry are located on substantially the same straight line.

12 Claims, 2 Drawing Sheets

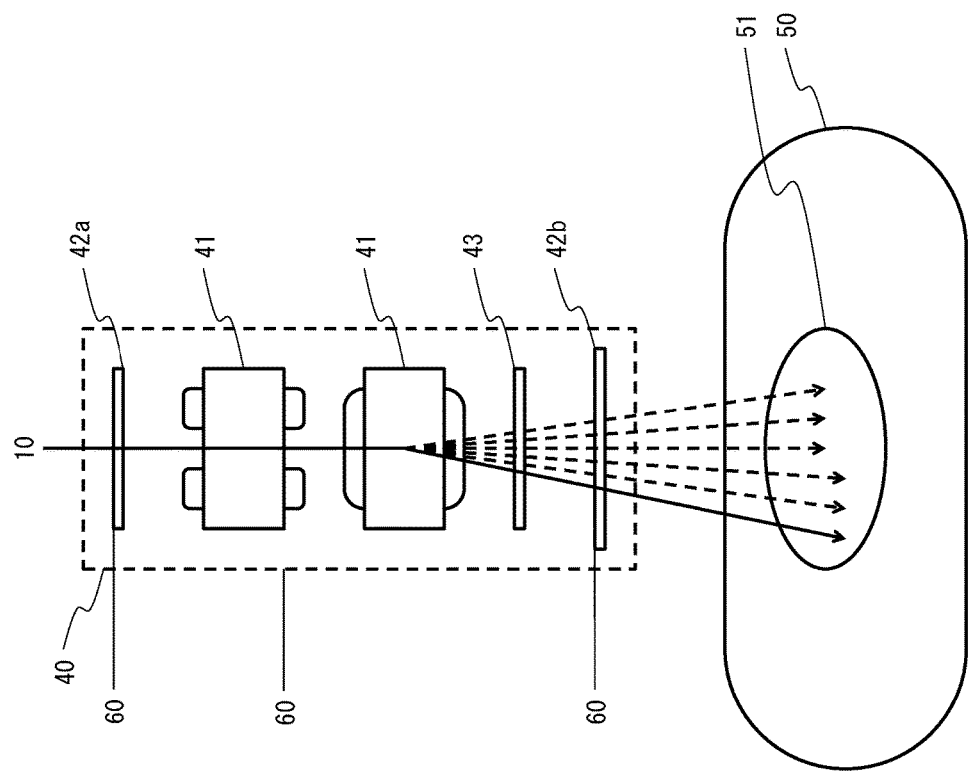

PARTICLE THERAPY SYSTEM

TECHNICAL FIELD

The present invention relates to a particle therapy system.

BACKGROUND ART

As a background art of this technical field, there is PTL 1. This official gazette describes as follows. "A momentum dispersion function refers to a correlation function between momentum and position, and there is a correlation between momentum and position in a charged particle beam extracted from an accelerator system 2, and therefore, in order to ensure the treatment quality, it is important to eliminate this correlation when it is transported to the entrance of a gantry. The role of the beam transport system 3 is not only to transport a charged particle beam to a gantry 5, but also to eliminate the momentum dispersion function and perform the transport. In general, when momentum dispersion has occurred in the x direction in the accelerator, it is necessary to combine an x-direction bending magnet with a quadrupole magnet so as to cancel the dispersion in the x direction, and when momentum dispersion has occurred in the y direction in the extraction from the accelerator, it is necessary to combine a y-direction bending magnet with a quadrupole magnet so as to cancel the dispersion in the y direction. There are various systems in the extraction system from the accelerator, however, among them, some have a property in which time and momentum distribution have a strong correlation, that is, some have a tendency that the central momentum greatly changes with time. This is considered to be due to a cyclic variation in the magnetic field of the magnet in the above-mentioned accelerator or radiofrequency power, or the like, and as described in first to fifth embodiments, such a cyclic variation, that is, the strong correlation between time and momentum distribution can be eliminated by monitoring the cyclic variation linked with the operational cycle of the accelerator on a beam position monitor, and performing orbit correction so as to cancel a dynamic variation in the output of the beam position monitor".

Further, this official gazette describes as follows. "In a case where there is a strong correlation between time and momentum in this manner, by combining a monitor with a dynamic steering magnet, the bending magnet can be omitted as compared with the conventional combination of a bending magnet with a quadrupole magnet, and a transport path having a momentum dispersion function of 0 can be realized by a small and inexpensive device".

CITATION LIST

Patent Literature

[PTL 1] WO 2013/069379

SUMMARY OF INVENTION

Technical Problem

In the particle therapy system described in PTL 1, the excitation amount of the steering magnet installed in a beam transport system (hereinafter referred to as "high energy beam transport system") from the exit of the synchrotron to the entrance of the rotating gantry is cyclically controlled so that a variation in the beam orbit at the entrance of the rotating gantry is corrected, and therefore, even if a bending magnet is omitted from the high energy beam transport system, the momentum dispersion function (hereinafter referred to as "dispersion") at the entrance of the rotating gantry is falsely corrected to 0, and thus, a variation in the irradiation beam position can be suppressed.

On the other hand, in the particle therapy system described in PTL 1, in a case where a component which is not cyclic (for example, a component which depends on the time pattern of the beam irradiation) is contained in the variation in the beam orbit at the entrance of the rotating gantry, the dispersion at the entrance of the rotating gantry cannot be corrected to 0. Therefore, it is difficult to sufficiently suppress a variation in the irradiation beam position in the particle therapy system described in PTL 1.

In view of this, the present invention provides a particle therapy system capable of reducing the installation area and also suppressing a variation in the irradiation beam position.

Solution to Problem

In order to solve the above problem, for example, the configuration described in the claims is adopted. This application includes a plurality of means for solving the above problem, however, examples thereof include a particle therapy system including a synchrotron which generates a charged particle beam, a beam delivery system which irradiates an irradiation target with the charged particle beam extracted from the synchrotron thereby forming a radiation field, a rotating gantry which is provided with the beam delivery system and is rotatable around the irradiation target, and a dispersion measuring device which measures the dispersion of the charged particle beam at the position of the irradiation target at a plurality of rotation angles of the rotating gantry, wherein the orbit center of the charged particle beam extracted from the synchrotron and the rotation axis of the rotating gantry are located on substantially the same straight line.

Advantageous Effects of Invention

According to the invention, a particle therapy system capable of reducing the installation area and also suppressing a variation in the irradiation beam position can be provided.

Objects, configurations, and effects other than those described above will be clarified by the description of the following embodiments.

BRIEF DESCRIPTION OF DRAWINGS

FIG. 2 is a schematic view of a beam delivery system 40 of the first embodiment.

DESCRIPTION OF EMBODIMENTS

Figure 1:
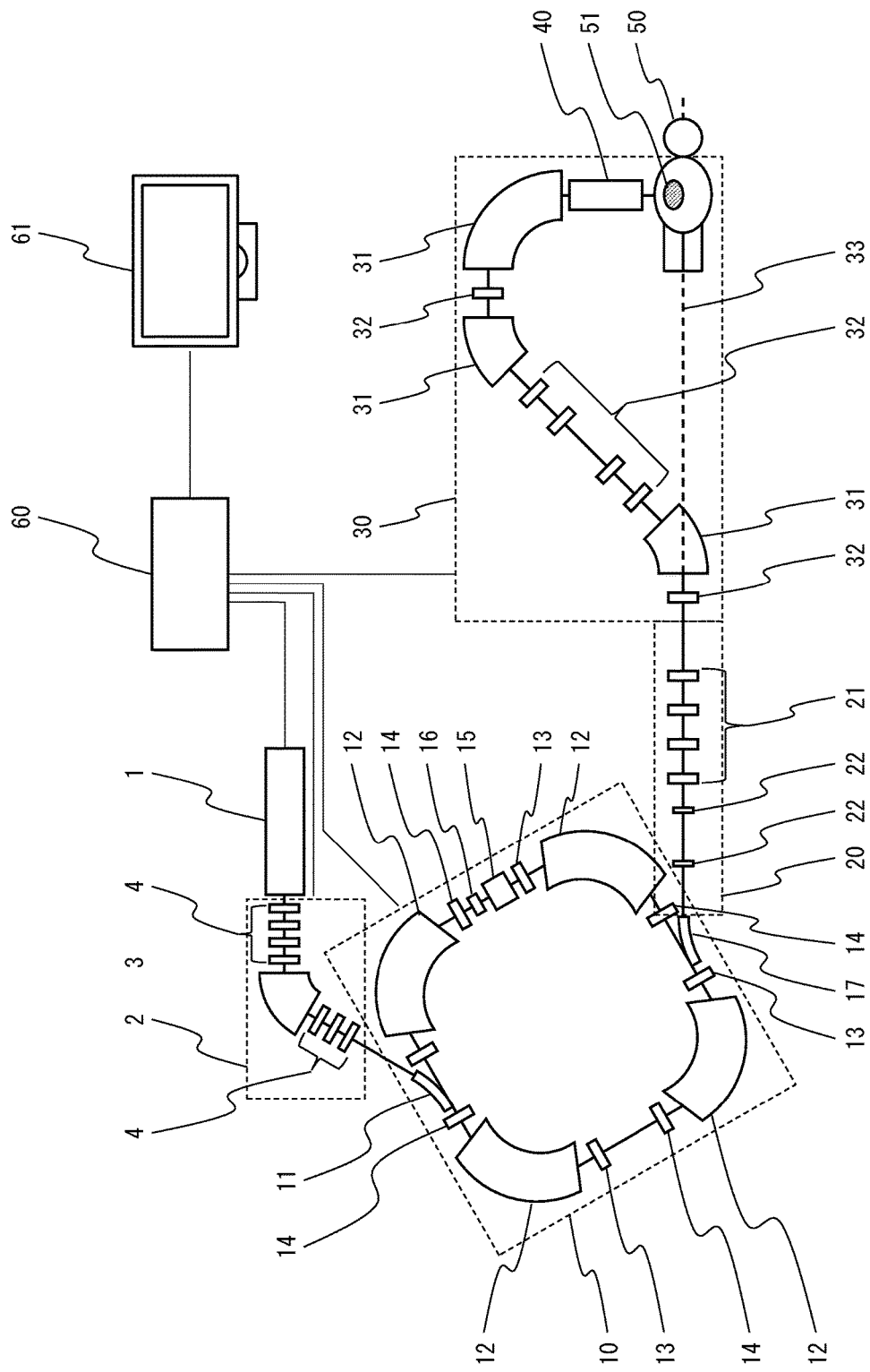
FIG. 1 shows an example of a particle therapy system of a first embodiment.

Hereinafter, preferred embodiments of the invention will be described with reference to the drawings.

In this embodiment, an example of a particle therapy system capable of reducing the installation area and also suppressing a variation in the irradiation beam position over a plurality of operation cycles of a synchrotron will be described.

FIG. 1 shows an example of a particle therapy system according to this embodiment.

The particle therapy system of this embodiment accelerates a charged particle beam (hereinafter referred to as "beam") injected into a synchrotron 10 by an injector 1 to a predetermined kinetic energy (hereinafter, the kinetic energy is simply referred to as "energy") by the synchrotron 10, and extracts the beam to a high energy beam transport system 20, and then irradiates an affected part 51 of a patient 50 with the beam through a rotating gantry 30 and a beam delivery system 40 mounted on the rotating gantry 30. As the injector 1, for example, a linear accelerator (LINAC) which accelerates a beam generated by an ion source (not shown) to an energy suitable for injection (hereinafter referred to as "injection energy") into the synchrotron 10 is used.

The charged particle beam extracted from the injector 1 is injected into the synchrotron 10 through a low energy beam transport system 2 and an inflector for injection 11. The low energy beam transport system 2 is constituted by a bending magnet 3 which bends the beam toward the synchrotron 10, a quadrupole magnet 4 which makes the shape of the beam into a shape suitable for injection into the synchrotron 10, etc.

The synchrotron 10 is constituted by the inflector for injection 11, a bending magnet 12, a quadrupole magnet 13, a sextupole magnet 14, a radiofrequency acceleration cavity 15, a radiofrequency voltage application device for extraction 16, and a deflector for extraction 17.

The bending magnet 12 bends a beam which circulates in the synchrotron 10 (hereinafter referred to as "circulating beam") to form a predetermined circulating orbit (hereinafter referred to as "circulating beam orbit"). The direction along the traveling direction of the circulating beam is referred to as "traveling direction" (the direction in which the beam travels is defined to be positive), the direction vertical to the traveling direction and along the radial direction of the bending magnet 12 is referred to as "horizontal direction" (the outward direction of the synchrotron is defined to be positive), and the direction vertical to both the traveling direction and the horizontal direction is referred to as "vertical direction" (the front direction of the drawing is defined to be positive). The design circulating beam orbit of the synchrotron 10 is referred to as "central orbit". A circulating beam particle oscillates in the horizontal and vertical directions around the central orbit, and this oscillation is referred to as "betatron oscillation". Further, the frequency of betatron oscillation per synchrotron cycle is referred to as "tune". The quadrupole magnet 13 applies a convergence or divergence force to the circulating beam to maintain the tune of the circulating beam at such a value that the circulating beam becomes stable. The radiofrequency acceleration cavity 15 applies a radiofrequency voltage (hereinafter referred to as "acceleration voltage") in the traveling direction to the circulating beam to capture the circulating beam at a predetermined phase (hereinafter referred to as "radiofrequency capture") in the traveling direction, and accelerate the circulating beam to a predetermined energy. As for the momentum of the circulating beam particle subjected to radiofrequency capture, the beam oscillates around the design momentum (hereinafter referred to as "central momentum"), and this oscillation is referred to as "synchrotron oscillation". While the circulating beam is accelerated, the excitation amount of the bending magnet 12 and the excitation amount of the quadrupole magnet 13 are increased in proportion to the momentum of the circulating beam, and also the frequency of the acceleration voltage (hereinafter referred to as "acceleration frequency") is controlled to an appropriate value, and the circulating beam orbit and the tune of the circulating beam are kept constant.

After the acceleration of the circulating beam is completed, the synchrotron 10 changes the excitation amount of the quadrupole magnet 13 to approximate the horizontal tune of the circulating beam to such a value that the circulating beam becomes unstable (hereinafter referred to as "resonance line"), and also excites the sextupole magnet 14 to apply a magnetic field (hereinafter referred to as "sextupole magnetic field") with an intensity in proportion to the square of the distance from the central orbit to the circulating beam, and thus forms the stability limit (hereinafter referred to as "separatrix") of the horizontal betatron oscillation in a phase space defined by the position and gradient in the horizontal direction of the circulating beam particle. The radiofrequency voltage application device for extraction 16 applies a radiofrequency voltage in the horizontal direction with a frequency synchronizing with the horizontal tune to the circulating beam to increase the amplitude of the horizontal betatron oscillation of the circulating beam particle. The circulating beam particle in which the amplitude of the horizontal betatron oscillation is increased and exceeds the separatrix rapidly increases the amplitude of the horizontal betatron oscillation and is injected into the deflector for extraction 17. The deflector for extraction 17 bends the injected circulating beam particle in the horizontal direction and is extracted outside the synchrotron 10. In this embodiment, a septum magnet which bends the beam in the horizontal direction is used as the deflector for extraction 17. Further, a lambertson magnet which bends the beam in the vertical direction can also be used as the deflector for extraction. In addition, the deflector for extraction 17 can also be constituted by a plurality of magnets or a combination of an electrostatic deflector which bends the beam by an electric field with a magnet. As the magnet constituting the deflector for extraction 17 in combination with the electrostatic deflector, one magnet or a plurality of magnets may be used.

The beam extracted from the synchrotron 10 (hereinafter referred to as "extracted beam") is irradiated onto the affected part 51 after passing through the high energy beam transport system 20, the rotating gantry 30, and the beam delivery system 40 on the rotating gantry 30. Incidentally, as shown in FIG. 1, in the particle therapy system of this embodiment, the orbit center of the beam extracted from the synchrotron 10 and the rotation axis of the rotating gantry 30 are located on substantially the same straight line. The high energy beam transport system 20 is constituted by a quadrupole magnet 21 which is a quadrupole magnetic field generator that generates a magnetic field for applying a convergence or divergence force to the extracted beam, a beam profile monitor 22 which measures the position or shape of the extracted beam, etc., and the end of the high energy beam transport system 20 is connected to the entrance of the rotating gantry 30. The start point of the high energy beam transport system 20, that is, the exit of the synchrotron 10 is defined as the start point of a linear portion where the exit of the deflector for extraction 17, that is, the quadrupole magnet 21 is installed, and in a case where the deflector for extraction 17 is constituted by a plurality of magnets, the exit point of the magnet located on the most downstream side is defined as the start point of the high energy beam transport system 20. Incidentally, the coordinate system in the high energy beam transport system 20 conforms to the coordinate system of the synchrotron 10, and a direction parallel to the horizontal plane of the synchrotron 10 in a plane vertical to the beam traveling direction becomes the horizontal direction, and a direction parallel to the gap direction of the bending magnet 12 becomes the vertical direction.

The rotating gantry 30 is constituted by a bending magnet 31, a quadrupole magnet 32, etc., and an end portion thereof is mounted with the beam delivery system 40. The rotating gantry 30 is configured such that the whole body thereof can rotate around a rotation axis 33, and can irradiate the affected part 51 with the beam injected from the high energy beam transport system 20 from a plurality of different directions. Incidentally, as described above, in the particle therapy system of this embodiment, the orbit center of the beam extracted from the synchrotron 10 and the rotation axis of the rotating gantry 30 are located on substantially the same straight line, and therefore, the high energy beam transport system 20 is provided on a line extending from the rotation axis 33. Therefore, the high energy beam transport system 20 of this embodiment may also be referred to as a device which linearly transports the extracted beam from the synchrotron 10 to the rotating gantry 30.

Next, when explaining the particle therapy system of this embodiment, as the definition of a word, an angle formed by the beam traveling direction in the beam delivery system 40 and the horizontal plane of a treatment room in which the patient 50 is present is referred to as "gantry rotation angle". Further, a point on which the beams irradiated from a plurality of directions gather in the affected part 51 is referred to as "isocenter". In the coordinate system in the rotating gantry 30, the radial direction of the bending magnet 31 becomes the horizontal direction, and the gap direction of the bending magnet 31 becomes the vertical direction.

The coordinate system in the rotating gantry 30 rotates accompanying the rotation of the rotating gantry 30, and in a case where the gantry rotation angle is 0°, that is, in a case where the bending magnet 31 bends the beam in the horizontal direction of the high energy beam transport system 20, the coordinate system of the high energy beam transport system 20 and the coordinate system of the rotating gantry 30 coincide with each other at the entrance of the rotating gantry 30. Further, in this embodiment, a bending magnet is not installed in the high energy beam transport system 20, and therefore, the rotation axis 33 of the rotating gantry 30 is substantially the same as the beam traveling direction at the exit point of the deflector for extraction 17, that is, the exit of the synchrotron 10.

The constituent devices of the injector 1, the low energy beam transport system 2, the synchrotron 10, the high energy beam transport system 20, and the rotating gantry 30, and a power supply (not shown) which supplies electric power to these constituent devices are connected to a control system 60, and the control system 60 controls the operation of these devices. Further, the control system is connected to a terminal 61 for performing display of the input and output of the operational information or the operational state.

FIG. 2 is a schematic view of the beam delivery system 40. The beam delivery system 40 includes a scanning magnet 41, beam profile monitors 42a and 42b, each of which measures the position, width, or shape of the beam, and a dose monitor 43 which measures the irradiation dose of the beam as main devices, and the devices which constitute the beam delivery system 40 are connected to the control system 60. The beam delivery system 40 fixes the shape of the beam transported through the high energy beam transport system 20 and the rotating gantry 30, and forms an irradiation dose distribution (hereinafter referred to as "radiation field") according to the shape of the affected part 51. In the particle therapy system of this embodiment, a scanning irradiation method in which the beam is scanned according to the shape of the affected part 51 by the scanning magnet 41 is used for forming the radiation field. Further, the beam delivery system 40 is fixed to the rotating gantry 30, and therefore is configured to be able to irradiate an irradiation target with the beam from an arbitrary angle by rotating the rotating gantry 30.

In the scanning irradiation method, a depth to which the beam reaches in the body of the patient 50 is controlled by changing the energy of the beam to be irradiated onto the patient 50. In this embodiment, in order to change the energy of the beam to be irradiated onto the patient 50, the energy of the beam to be extracted from the synchrotron 10 is changed.

After the extraction of the circulating beam is completed, the synchrotron 10 prepares for the next beam injection by changing the excitation amount of the bending magnet 12, the excitation amount of the quadrupole magnet 13, and the acceleration frequency to the values when the beam is injected into the synchrotron 10. A period from when the beam is injected into the synchrotron 10 to when the beam is injected into the synchrotron 10 next time is referred to as "the cycle of the synchrotron 10".

The particle therapy system of this embodiment repeats acceleration, extraction, and irradiation of the beam until the irradiation of the beam previously determined by a treatment planning system (not shown) is completed.

In the particle therapy system of this embodiment, a method for suppressing a variation in the irradiation beam position will be described.

The beam position in the horizontal and vertical directions at the isocenter varies as the central momentum of the beam to be extracted from the synchrotron 10 changes with time. At this time, it is known that there is a proportional relationship between the amount of change in the momentum and the amount of change in the beam position, and the constant of proportion between these is referred to as "dispersion". When the amount of change in the momentum is denoted by $\Delta p$, the central momentum of the beam is denoted by $p$, and the amount of change in the beam position is denoted by $\Delta x$, the dispersion $\eta$ is represented as follows.

(Numerical Formula 1)

$$\Delta x = \eta \frac{\Delta p}{p} \qquad \text{[Math 1]}$$

Incidentally, the dispersion is defined for each of the horizontal and vertical directions at each point in the beam traveling direction.

The value of the dispersion at the isocenter changes depending on the device arrangement of the high energy beam transport system 20 and the rotating gantry 30 and the excitation amounts of the quadrupole magnets 21 and 32. In a case where the dispersion at the isocenter becomes 0, a variation in the irradiation beam position accompanying a variation in the momentum of the beam also becomes 0, and therefore, it becomes possible to suppress the variation in the irradiation beam position by adjusting the excitation amounts of the quadrupole magnets 21 and 32 so that the dispersion at the isocenter becomes 0. In the particle therapy system of this embodiment, in a test run of the particle therapy system (hereinafter referred to as "beam adjustment"), the dispersion at the isocenter is measured, and the adjustment of the excitation amounts of the quadrupole magnets 21 and 32 is performed.

A method in which the dispersion at the isocenter is measured and the excitation amounts of the quadrupole magnets 21 and 32 are adjusted so that the dispersion at the isocenter becomes 0 in the beam adjustment will be described.

An adjusting person sets the gantry rotation angle to 0°, and thereafter sets the operation conditions (the excitation amount of the magnet and the acceleration frequency) of the device during beam irradiation to designed values for the energy as an adjustment target. At this time, information including the energy as an adjustment target, the acceleration frequency of the synchrotron 10 during extraction of the beam, and the gantry rotation angle is displayed on the terminal 61.

Subsequently, the adjusting person operates the synchrotron 10, and measures the position of the irradiation beam at the isocenter using the profile monitors 42a and 42b. At this time, the excitation current of the scanning magnet 41 has been set to 0. In the beam delivery system 40, a device which bends the beam is not installed other than the scanning magnet 41, and therefore, the horizontal beam position x0 at the isocenter is represented as follows using xa0 which denotes the measurement result of the horizontal beam position by the profile monitor 42a, sa which denotes a distance from the profile monitor 42a to the isocenter, xb0 which denotes the measurement result of the horizontal beam position by the profile monitor 42b, and sb which denotes a distance from the profile monitor 42b to the isocenter.

(Numerical Formula 2)

$$x_0 = \frac{s_a x_{b0} - s_b x_{a0}}{s_a - s_b} \quad [\text{Math 2}]$$

In this embodiment, the beam position at the isocenter is calculated from the measurement results of the beam position by the two profile monitors 42a and 42b in the beam delivery system 40, however, the beam position at the isocenter may be directly measured by installing a profile monitor for adjustment in the isocenter during the beam adjustment period.

After the measurement of the beam position at the isocenter is completed, the adjusting person changes the acceleration frequency of the synchrotron 10 from the designed value and changes the energy of the circulating beam of the synchrotron 10, that is, the momentum of the beam to be extracted from the synchrotron 10. In a case where there is no change in the magnetic field intensity of the bending magnet 12 of the synchrotron 10, there is the following relationship between the amount of change in the acceleration frequency Δf and the amount of change in the momentum Δp.

(Numerical Formula 3)

$$\frac{\Delta p}{p} = \frac{\gamma^2}{1 - \alpha \gamma} \frac{\Delta f}{f} \quad [\text{Math 3}]$$

Here, p denotes the momentum of the circulating beam particle, f denotes the acceleration frequency, γ denotes the Lorentz factor of the circulating beam particle, and α denotes the momentum compaction factor of the synchrotron 10. According to the (numerical formula 3), there is a proportional relationship between the amount of change in the acceleration frequency and the amount of change in the momentum, and therefore, the adjusting person can know the amount of change in the momentum of the irradiation beam from the set value of the acceleration frequency displayed on the terminal 61. Further, the control system 60 may calculate the amount of change in the momentum Δp/p from the acceleration frequency and the parameter of the synchrotron 10 and display the calculated amount on the terminal 61.

The adjusting person measures the horizontal beam position x1 at the isocenter in a state where the acceleration frequency of the synchrotron 10 is changed, and obtains the horizontal dispersion ηx0 at the isocenter when the gantry rotation angle is 0° from the amount of change in the horizontal beam position.

(Numerical Formula 4)

$$\eta_{x0} = \frac{x_1 - x_0}{\Delta p / p} \quad [\text{Math 4}]$$

The vertical dispersion ηy0 at the isocenter when the gantry rotation angle is 0° is obtained from the measurement result of the beam position in the same manner as the horizontal dispersion. The adjusting person records the horizontal dispersion ηx0 and the vertical dispersion ηy0 when the gantry rotation angle is 0° along with the gantry rotation angle (0°) at the time of measurement.

Subsequently, the adjusting person changes the gantry rotation angle to 90°, performs the measurement in the same manner, and records the horizontal dispersion ηx90 and the vertical dispersion ηy90 when the gantry rotation angle is 90° along with the gantry rotation angle (90°) at that time. In this manner, the particle therapy system of this embodiment includes a means for knowing the momentum shift of the beam extracted from the synchrotron 10 (in this embodiment, the terminal 61 which displays the acceleration frequency), a means for knowing the gantry rotation angle (in this embodiment, the terminal 61 which displays the gantry rotation angle), and a means for measuring the beam position at the isocenter (in this embodiment, the profile monitors 42a and 42b), and therefore, the dispersion at the isocenter can be recorded in association with the gantry rotation angle. In other words, the dispersion measuring device of this embodiment is constituted by a means for knowing the momentum shift of the beam extracted from the synchrotron 10, a means for knowing the gantry rotation angle, and a means for measuring the beam position at the isocenter.

The horizontal dispersion and the vertical dispersion at the exit of the synchrotron 10 are denoted by ηxs and ηys, respectively, and the changing ratio of the horizontal dispersion and the changing ratio of the vertical dispersion using the position in the beam traveling direction as a variable are denoted by ηxs' and ηys', respectively. The changing ratio along the beam traveling direction of the dispersion is referred to as "gradient". As the dispersion and the gradient thereof, the design values of the synchrotron 10 may be used, or these may be derived from the measurement result of the beam position by the beam profile monitor 22 in the high energy beam transport system 20.

When the transport matrix in the horizontal direction and the transport matrix in the vertical direction of the high energy beam transport system 20 are denoted by Hx and Hy, respectively, and the transport matrix in the horizontal direction and the transport matrix in the vertical direction of the rotating gantry 30 are denoted by Gx and Gy, respectively, the dispersion at the isocenter is represented by the following formula.

(Numerical Formula 5)

$$\eta_{x0} = \left(G_x H_x \begin{pmatrix} \eta_{xs} \\ \eta'_{xs} \end{pmatrix}\right)_1$$

$$\eta_{y0} = \left(G_y H_y \begin{pmatrix} \eta_{ys} \\ \eta'_{ys} \end{pmatrix}\right)_1$$

$$\eta_{x90} = \left(G_x H_y \begin{pmatrix} \eta_{ys} \\ \eta'_{ys} \end{pmatrix}\right)_1$$

$$\eta_{y90} = \left(G_y H_x \begin{pmatrix} \eta_{xs} \\ \eta'_{xs} \end{pmatrix}\right)_1$$

[Math 5]

The subscript 1 on the right side of the (numerical formula 5) indicates that the first column vector to be a calculation result becomes the dispersion. The second column vector becomes the gradient of the dispersion, however, in this embodiment, the gradient of the dispersion at the isocenter is not an adjustment target, and therefore, the expression in the (numerical formula 5) is omitted.

Assuming that the excitation amount of the quadrupole magnet 32 in the rotating gantry 30 has been set so that with respect to the dispersion occurring in the rotating gantry 30, the value thereof at the isocenter becomes 0, that is, an achromatic condition is satisfied, a 2×2 matrix is considered as the transport matrix of the high energy beam transport system and the rotating gantry. The dispersion of the beam extracted from the synchrotron 10 and the gradient thereof have a non-zero value at least in the horizontal direction, and a bending magnet is not installed in the high energy beam transport system 20, and therefore, both the horizontal dispersion and the gradient thereof at the entrance of the rotating gantry 30 do not become 0.

In the rotating gantry which satisfies a general achromatic condition, in a case where both the dispersion and the gradient thereof at the entrance of the rotating gantry are 0, it is guaranteed that the dispersion and the gradient thereof at the isocenter become 0. On the other hand, in the particle therapy system of this embodiment, both the dispersion and the gradient thereof at the entrance of the rotating gantry 30 do not become 0, and therefore, the dispersion at the isocenter cannot be made 0 only by making the rotating gantry satisfy an achromatic condition.

In this embodiment, in addition that the rotating gantry 30 is made to satisfy an achromatic condition, the excitation amounts of the quadrupole magnets 21 and 32 on the high energy beam transport system 20 and the rotating gantry 30 are adjusted so that the transport matrix when the gantry rotation angle is 0° satisfies the following formula.

(Numerical Formula 6)

$$-\eta_{x0} = \left((G_{xC} H_{xC} - G_x H_x) \begin{pmatrix} \eta_{xS} \\ \eta'_{xS} \end{pmatrix}\right)_1$$

[Math 6]

Here, HxC denotes the transport matrix in the horizontal direction of the high energy beam transport system 20 after adjustment, and GxC denotes the transport matrix in the horizontal direction of the rotating gantry 30 after adjustment. The right side of the (numerical formula 6) gives the amount of change in the horizontal dispersion by the adjustment of the excitation amounts of the quadrupole magnets 21 and 32. According to the (numerical formula 6), the amount of change in the horizontal dispersion becomes a value obtained by changing the sign of the measurement result of the horizontal dispersion to the opposite sign, and therefore, by adjusting the excitation amounts of the quadrupole magnets 21 and 32 so as to satisfy the (numerical formula 6), the horizontal dispersion at the isocenter when the gantry rotation angle is 0° can be corrected to 0. It is also possible to correct the vertical dispersion when the gantry rotation angle is 0°, and the horizontal and vertical dispersions when the gantry rotation angle is 90° to 0 in the same manner. Further, it is possible to simultaneously correct the horizontal and vertical dispersions at a plurality of gantry rotation angles (0° and 90°) to 0 by adjusting the excitation amounts of the quadrupole magnets 21 and 32 so as to simultaneously satisfy the conditions corresponding to the (numerical formula 6) for each dispersion.

That is, in the particle therapy system of this embodiment, with respect to the dispersion of the beam extracted from the accelerator (synchrotron 10), the magnetic field in a path through which the beam passes is controlled so that the dispersion at the isocenter becomes 0 at a plurality of gantry rotation angles when the rotating gantry 30 satisfies an achromatic condition, and also the high energy beam transport system 20 and the rotating gantry 30 are combined.

In this embodiment, in order to extract the beam in the horizontal direction from the synchrotron 10, the vertical dispersion ηys at the exit of the deflector for extraction and the gradient thereof ηys' both become 0 because of the symmetry in the vertical direction of the synchrotron 10. In this case, by adjusting the excitation amounts of the quadrupole magnets 21 and 32 so as to satisfy the following formula in addition to the (numerical formula 6), the horizontal and vertical dispersions at a plurality of gantry rotation angles (0° and 90°) are simultaneously corrected to 0.

(Numerical Formula 7)

$$-\eta_{y90} = \left((G_{yC} H_{xC} - G_y H_x) \begin{pmatrix} \eta_{xs} \\ \eta'_{xs} \end{pmatrix}\right)_1$$

[Math 7]

Here, GyC denotes the transport matrix in the vertical direction of the rotating gantry 30 after adjustment.

In a case where the horizontal and vertical dispersions at a plurality of gantry rotation angles (0° and 90°) are simultaneously corrected to 0, the correction of the horizontal and vertical dispersions at the isocenter at an arbitrary gantry rotation angle to 0 will be described.

When the gantry rotation angle is an arbitrary value θ, the horizontal dispersion ηxθ at the isocenter is represented as follows using ηxθG which denotes the horizontal dispersion on the coordinate system of the rotating gantry 30 at the entrance of the rotating gantry 30 and ηxθG' which denotes the gradient thereof.

(Numerical Formula 8)

$$\eta_{x\theta} = \left(G_{xC} \begin{pmatrix} \eta_{x\theta G} \\ \eta'_{x\theta G} \end{pmatrix}\right)_1$$

[Math 8]

Here, the horizontal dispersion $\eta x\theta G$ on the coordinate system of the rotating gantry 30 and the gradient thereof $\eta x\theta G'$ are represented as follows using $\eta xH$ which denotes the horizontal dispersion on the coordinate system of the high energy beam transport system 20 at the entrance of the rotating gantry 30, $\eta xH'$ which denotes the gradient thereof, $\eta yH$ which denotes the vertical dispersion, $\eta yH'$ which denotes the gradient thereof, and the gantry rotation angle $\theta$.

$$\eta_{x\theta G} = \eta_{xH} \cos\theta + \eta_{yH} \sin\theta$$

$$\eta'_{x\theta G} = \eta'_{xH} \cos\theta + \eta'_{yH} \sin\theta \qquad \text{[Math 9]}$$

(Numerical Formula 9)

Here, the following equation is satisfied.

(Numerical Formula 10)

$$\begin{pmatrix} \eta_{xH} \\ \eta'_{xH} \end{pmatrix} = H_{xc} \begin{pmatrix} \eta_{xS} \\ \eta'_{xS} \end{pmatrix} \qquad \text{[Math 10]}$$

Therefore, from the (numerical formula 6), the (numerical formula 8), and the (numerical formula 9), it is shown that the following equation is satisfied.

(Numerical Formula 11)

$$\eta_{x\theta} = \left( G_{xC} H_{xC} \begin{pmatrix} \eta_{xS} \\ \eta'_{xS} \end{pmatrix} \right)_1 \cos\theta = 0 \qquad \text{[Math 11]}$$

In the same manner, it is shown that also the vertical dispersion $\eta y\theta$ at the isocenter becomes 0 at an arbitrary gantry rotation angle $\theta$.

In this manner, in the particle therapy system of this embodiment, the dispersions at the isocenter at a plurality of gantry rotation angles are measured, and the excitation amounts of the quadrupole magnet 21 in the high energy beam transport system 20 and the quadrupole magnet 32 in the rotating gantry 30 are adjusted so as to correct these dispersions to 0, and therefore, it becomes possible to correct the dispersion at the isocenter at an arbitrary gantry rotation angle to 0 without installing a bending magnet in the high energy beam transport system 20.

Accordingly, the particle therapy system of this embodiment can reduce the installation area and also suppress a variation in the irradiation beam position.

In this embodiment, the excitation amounts of the quadrupole magnets 21 and 32 are adjusted so that the dispersion at the isocenter becomes 0, however, in fact, by correcting the dispersion at the isocenter within such a range that a variation in the irradiation beam position accompanying a variation in the momentum of the beam falls within a tolerance range for forming a radiation field, the effect of this embodiment that a variation in the irradiation beam position is suppressed can be obtained. It has been found from an analysis that the central momentum of the beam extracted from the synchrotron 10 varies by about 0.01% in the whole width as an example. The tolerance range of the variation width of the irradiation beam position in the scanning irradiation method is, for example, 0.5 mm, and therefore, the absolute value of the dispersion at the isocenter may be corrected so that the amount of change in the beam position when the momentum of the beam changes by 0.01% is 0.5 mm or less.

Further, in the above-mentioned embodiment, a system in which a so-called full gantry capable of rotating at 360 degrees is adopted as the rotating gantry 30 is described as an example, however, the system is not limited thereto, and a system in which a rotating gantry whose rotation angle is less than 360 degrees is used may be adopted.

Further, in the above-mentioned embodiment, an example in which the beam delivery system 40 adopts a scanning irradiation method is mainly described, however, the invention may be applied without being limited to the particle therapy system which can perform only this irradiation method. For example, the invention can also be applied to a case where the beam delivery system 40 is configured to be able to perform irradiation by switching between a scatterer irradiation method and a scanning irradiation method, or the like.

Incidentally, the particle therapy system described in the above-mentioned embodiment is an example of the invention, and a device required for controlling the installation position of a device or the number of devices, or another particle therapy system may be added within a scope capable of achieving the object of the invention.

REFERENCE SINGS LIST

1: injector
2: low energy beam transport system
3: bending magnet
4: quadrupole magnet
10: synchrotron
11: inflector for injection
12: bending magnet
13: quadrupole magnet
14: sextupole magnet
15: radiofrequency acceleration cavity
16: radiofrequency voltage application device for extraction
17: deflector for extraction
20: high energy beam transport system
21: quadrupole magnet
22: beam profile monitor
30: rotating gantry
31: bending magnet
32: quadrupole magnet
33: rotation axis
40: beam delivery system
41: scanning magnet
42a, 42b: beam profile monitor
43: dose monitor
50: patient
51: affected part
60: control system
61: terminal

The invention claimed is:
1. A particle therapy system, comprising:
a synchrotron which generates a charged particle beam;
a beam delivery system which irradiates an irradiation target with a charged particle beam extracted from the synchrotron thereby forming a radiation field;
a rotating gantry which is provided with the beam delivery system and is rotatable around the irradiation target; and
a dispersion measuring device which measures the dispersion of the charged particle beam at the position of the irradiation target at a plurality of rotation angles of the rotating gantry, wherein the orbit center of the charged particle beam extracted from the synchrotron and the rotation axis of the rotating gantry are located on substantially the same straight line, and wherein the charged particle beam has vertical and horizontal dispersions at the plurality of rotation angles of the rotating gantry, and the vertical and horizontal dispersions are simultaneously corrected to zero.

2. The particle therapy system according to claim 1, wherein a high energy beam transport system which linearly transports the charged particle beam from the synchrotron to the rotating gantry is provided on a line extending from the rotation axis of the rotating gantry.

3. The particle therapy system according to claim 1, wherein the dispersion at the position of the irradiation target is adjusted using a quadrupole magnetic field generator.

4. The particle therapy system according to claim 3, wherein the dispersion at the position of the irradiation target is adjusted within such a range that the amount of change in the position of the beam at the position of the irradiation target when the momentum of the beam changes by 0.01% becomes 0.5 mm or less.

5. The particle therapy system according to claim 1, further comprising:

a deflector for extraction disposed at an exit of the synchrotron to receive the charged particle beam, the deflector for extraction including a first quadrupole magnet, wherein the defector for extraction is disposed between the exit of the synchrotron and an entry of the beam delivery system, wherein the beam delivery system includes a second quadrupole magnet, and wherein excitation amounts of the first and second quadrupole magnets are adjusted to correct the horizontal and vertical dispersions at the plurality of gantry rotations of the rotating gantry simultaneously to zero.

6. A particle therapy system, comprising:

a synchrotron which generates a charged particle beam;

a beam delivery system which irradiates an irradiation target with a charged particle beam extracted from the synchrotron thereby forming a radiation field;

a rotating gantry which is provided with the beam delivery system and is rotatable around the irradiation target; and a dispersion measuring device which measures the dispersion of the charged particle beam at the position of the irradiation target at a plurality of rotation angles of the rotating gantry, wherein the plurality of rotation angles of the rotating gantry include at least 0° and 90°, and wherein the orbit center of the charged particle beam extracted from the synchrotron and the rotation axis of the rotating gantry are located on substantially the same straight line.

7. The particle therapy system according to claim 6, wherein the charged particle beam has vertical and horizontal dispersions at the plurality of rotation angles of the rotating gantry, and the vertical and horizontal dispersions are simultaneously corrected to zero.

8. The particle therapy system according to claim 7, further comprising:

a deflector for extraction disposed at an exit of the synchrotron to receive the charged particle beam, the deflector for extraction including a first quadrupole magnet, wherein the defector for extraction is disposed between the exit of the synchrotron and an entry of the beam delivery system, wherein the beam delivery system includes a second quadrupole magnet, and wherein excitation amounts of the first and second quadrupole magnets are adjusted to correct the horizontal and vertical dispersions at the plurality of gantry rotations of the rotating gantry simultaneously to zero.

9. The particle therapy system according to claim 6, further comprising:

a deflector for extraction disposed at an exit of the synchrotron to receive the charged particle beam, the deflector for extraction including a first quadrupole magnet, wherein the defector for extraction is disposed between the exit of the synchrotron and an entry of the beam delivery system, wherein the beam delivery system includes a second quadrupole magnet, and wherein excitation amounts of the first and second quadrupole magnets are adjustable to change the horizontal and vertical dispersions at the plurality of gantry rotations of the rotating gantry.

10. The particle therapy system according to claim 6, further comprising:

a high energy beam transport system, which linearly transports the charged particle beam from the synchrotron to the rotating gantry, on a line extending from the rotation axis of the rotating gantry.

11. The particle therapy system according to claim 6, wherein the dispersion at the position of the irradiation target is adjusted using a quadrupole magnetic field generator.

12. The particle therapy system according to claim 11, wherein the dispersion at the position of the irradiation target is adjusted within such a range that the amount of change in the position of the beam at the position of the irradiation target when the momentum of the beam changes by 0.01% becomes 0.5 mm or less.

* * * * *